United States Patent [19]

Waldeck et al.

[11] Patent Number: 5,010,076
[45] Date of Patent: Apr. 23, 1991

[54] 1,7-FUSED 1H-INDOLE-2-CARBOXYLIC ACID-N-(1,4-BENZODIAZEPIN-3-YL)AMIDES

[75] Inventors: Harald Waldeck, Hanover; Werner Benson, Seelze; Horst Zeugner, Hanover; Klaus-Ullrich Wolf, Uetze; Peter-Colin Gregory, Hanover, all of Fed. Rep. of Germany; Derk Hamminga, Leusden, Netherlands; Ineke van Wijngaarden, Oud-Turnhout, Belgium

[73] Assignee: Kali-Chemie Pharma GmbH, Hanover, Fed. Rep. of Germany

[21] Appl. No.: 489,502

[22] Filed: Mar. 7, 1990

[30] Foreign Application Priority Data

Mar. 8, 1989 [DE]  Fed. Rep. of Germany ....... 3907389
Mar. 8, 1989 [DE]  Fed. Rep. of Germany ....... 3907390

[51] Int. Cl.$^5$ .................... C07D 521/00; A61K 31/55
[52] U.S. Cl. .................................... 514/221; 514/220; 540/495; 540/509
[58] Field of Search ................ 514/220, 221; 540/495, 540/509

[56] References Cited

U.S. PATENT DOCUMENTS

| 4,567,177 | 1/1986 | Bigg et al. | 514/214 |
| 4,628,084 | 12/1986 | Bock et al. | 540/509 |
| 4,820,834 | 4/1989 | Evans et al. | 540/504 |

FOREIGN PATENT DOCUMENTS

| 167919 | 4/1986 | European Pat. Off. | 540/509 |
| 322016 | 6/1989 | European Pat. Off. | 540/509 |
| 2567126 | 1/1986 | France | 514/214 |

OTHER PUBLICATIONS

Chemical Abstracts 105:107944z.
Chemical Abstracts 109:204385h.

Journal of Heterocyclic Chemistry, vol. 11, No. 3, pp. 387-393 (1974).

Primary Examiner—Robert T. Bond
Attorney, Agent, or Firm—Foley & Lardner

[57] ABSTRACT

Compounds corresponding to the formula I in which
- $R^1$ represents hydrogen, lower alkyl or cycloalkylalkyl with 4–7 carbon atoms,
- $R^2$ represents hydrogen, halogen, lower alkyl, lower alkoxy or trifluoromethyl, and
- $R^3$ represents hydrogen, halogen, lower alkyl or lower alkoxy, or
- $R^2$ and $R^3$ together denote an alkylenedioxy group,
- $R^4$ represents cycloalkyl with 5 to 6 carbon atoms, thiophene or optionally substituted phenyl,
- $R^5$ represents hydrogen or halogen,
- $R^6$ represents hydrogen, halogen, lower alkyl, lower alkoxy or trifluoromethyl, and
- Z represents an alkylene chain with 2–4 carbon atoms, which can optionally be mono- or disubstituted by lower alkyl or onto which a 5-6-membered carbocyclic ring can optionally be fused, or represents an —X—CH$_2$—CH$_2$— chain, which have pharmacologically valuable properties, are described, together with a method for their preparation.

10 Claims, No Drawings

1,7-FUSED 1H-INDOLE-2-CARBOXYLIC ACID-N-(1,4-BENZODIAZEPIN-3-YL)AMIDES

BACKGROUND OF THE INVENTION

The present invention relates to novel amides of 3-amino-1,4-benzodiazepine derivatives with 1,7-fused 1H-indole-2-carboxylic acid derivatives and the salts thereof, and pharmaceutical compositions containing these compounds and to a process for the preparation of these compounds.

European Patent Application No. 0,167,919 discloses 1,4-benzodiazepine derivatives which are substituted in the 3-position and have CCK-antagonistic effects.

Cholecystokinin (=CCK) is a peptide which occurs in gastrointestinal tissue and in the central nervous system, has a widely diverse spectrum of effects and which exerts, inter alia, stimulating effects on colon motility, gallbladder contraction and exocrine pancreas secretion and inhibitory effects on emptying of the stomach, and also influences appetite regulation. CCK antagonists are pharmacologically active substances which are able to bind to CCK receptors and thus can inhibit CCK-induced processes.

SUMMARY OF THE INVENTION

The object of the present invention is to develop novel compounds having CCK-antagonistic activity and an improved activity profile.

The invention furthermore has the object of preparing novel derivatives of 1,7-fused 1H-indole-2-carboxylic acids with valuable pharmacological properties.

These and other objects of the invention are achieved by providing a compound corresponding to the formula I

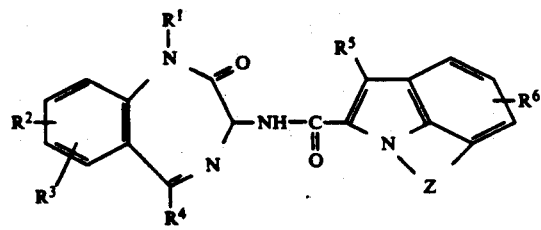

wherein
- $R^1$ represents hydrogen, lower alkyl or cycloalkylalkyl with 4–7 carbon atoms,
- $R^2$ represents hydrogen, halogen, lower alkyl, lower alkoxy or trifluoromethyl, and
- $R^3$ represents hydrogen, halogen, lower alkyl or lower alkoxy, or
- $R^2$ and $R^3$ are bonded to two adjacent carbon atoms and together denote an alkylenedioxy group with 1–2 carbon atoms,
- $R^4$ represents cycloalkyl with 5 to 6 carbon atoms, thiophene or an optionally substituted phenyl group a

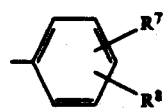

in which
- $R^7$ represents hydrogen, halogen, lower alkyl, lower alkoxy or trifluoromethyl, and
- $R^8$ represents hydrogen, halogen, lower alkyl or lower alkoxy,
- $R^5$ represents hydrogen or halogen,
- $R^6$ represents hydrogen, halogen, lower alkyl, lower alkoxy or trifluoromethyl, and
- Z represents an alkylene chain with 2–4 carbon atoms, which can optionally be mono- or disubstituted by lower alkyl, or onto which a 5–6-membered carbocyclic ring can optionally be fused, or represents a —X—CH$_2$—CH$_2$—chain in which X is bonded to the phenyl ring of the indole structure and represents oxygen or sulfur, and the acid addition salts thereof.

It has now been found that the 1,7-fused 1H-indole-2-carboxylic acid-N-(1,4-benzodiazepin-3-yl)-amides according to the invention have CCK-antagonistic properties and are distinguished by a novel type of pharmacological activity profile with a pronounced component of the effect promoting emptying of the stomach, along with a good therapeutic index and low toxicity.

DETAILED DESCRIPTION OF PREFERRED EMBODIMENTS

The present invention therefore relates to novel 1,7-fused 1H-indole-2-carboxylic acid-N-(1,4-benzodiazepin-3-yl)amide compounds corresponding to the formula I

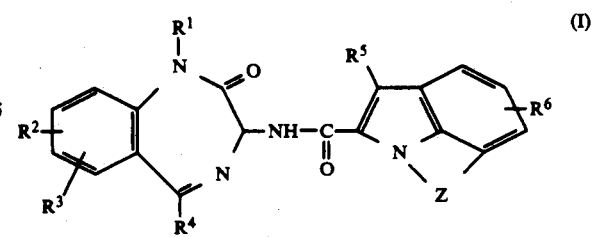

in which
- $R^1$ represents hydrogen, lower alkyl or cycloalkylalkyl with 4–7 carbon atoms,
- $R^2$ represents hydrogen, halogen, lower alkyl, lower alkoxy or trifluoromethyl, and
- $R^3$ represents hydrogen, halogen, lower alkyl or lower alkoxy, or
- $R^2$ and $R^3$ are bonded to two adjacent carbon atoms and together denote an alkylenedioxy group with 1–2 carbon atoms,
- $R^4$ represents cycloalkyl with 5 to 6 carbon atoms, thiophene or an optionally substituted phenyl group a

in which
- $R^7$ represents hydrogen, halogen, lower alkyl, lower alkoxy or trifluoromethyl, and
- $R^8$ represents hydrogen, halogen, lower alkyl or lower alkoxy,
- $R^5$ represents hydrogen or halogen,
- $R^6$ represents hydrogen, halogen, lower alkyl, lower alkoxy or trifluoromethyl, and represents an alkylene chain with 2-4 carbon atoms, which can optionally be mono- or disubstituted by lower alkyl, or onto which a 5-6-membered carbocyclic ring can optionally be fused, or represents an —X—CH$_2$—CH$_2$—chain in which X is bonded to the phenyl ring of the indole structure and represents oxygen or sulfur,
and the acid addition salts thereof.

R$^1$ in the compounds of formula I preferably represents a lower alkyl group. This can be straight chain or branched and preferably contain 1-4 carbon atoms. Cyclopropylmethyl may be mentioned as example of a cycloalkylalkyl group. Particularly suitable R$^1$ radicals have proved to be straight-chain and branched alkyl groups with 1-3 carbon atoms, especially methyl.

Where the substituents R$^2$, R$^3$ and R$^4$ in the compounds of formula I represent or contain a lower alkyl group, this can represent a straight or branched alkyl group with 1-5, preferably 1-4, carbon atoms, especially methyl or ethyl. Thus, lower alkyl substituents preferably represent methyl, and lower alkoxy substituents preferably represent methoxy. Halogen substituents R$^1$, R$^2$, R$^3$, R$^5$ and R$^6$ represent, in particular, fluorine, chlorine or bromine.

The substituents R$^2$ and R$^3$ are preferably located in the 7- and 8-positions of the benzodiazepine structure and preferably represent hydrogen, lower alkoxy, especially methoxy or lower alkyl, especially methyl, or else chlorine. A methoxy substituent in the 8-position has proved to be particularly advantageous.

The substituent R$^4$ preferably represents an optionally substituted phenyl group. The substituents R$^7$ and R$^8$ of the 5-phenyl group preferably represent hydrogen, lower alkyl, especially methyl, or halogen, especially fluorine or chlorine, or else lower alkoxy with 1-5 carbon atoms, for example isopentyloxy. A phenyl group R$^4$ which is unsubstituted or substituted by fluorine is particularly suitable.

If the substituent R$^4$ represents a cycloalkyl group, it is preferably cyclohexyl.

The substituent R$^6$ preferably represents hydrogen or else halogen, especially fluorine, or lower alkoxy, especially methoxy. The substituent R$^5$ preferably represents hydrogen. If R$^5$ represents halogen, it is preferably chlorine.

Z represents a chain with 2-4 chain members, preferably an alkylene chain with 2-4 carbon atoms. Thus Z forms with the aminoethylene group to which it is bonded a 5- to 7-membered heterocycle. Z preferably represents a propylene chain and thus forms together with the indole structure to which it is bonded a 4H-pyrrolo[3,2,1-ij]-5,6-dihydroquinoline structure. Where the alkylene chain Z is substituted by lower alkyl, this can contain 1-4 carbon atoms and represents, in particular, methyl. Where a carboxylic ring is fused onto the alkylene chain Z, this ring can be unsaturated or saturated and preferably represents a benzene ring.

The compounds of formula I contain an asymmetric carbon atom in the 3-position of the benzodiazepine structure and can exist in the D and the L forms or as racemate. The present invention embraces both the racemic mixtures and the pure optical isomers of the compounds of formula I.

The novel amides of formula I and the acid addition salts thereof are obtained according to the invention by acylating, in a known manner, amino compounds corresponding to the formula II

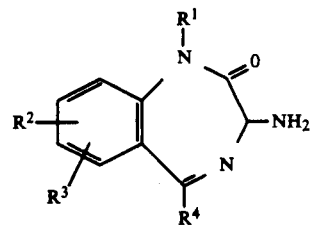

(II)

in which R$^1$, R$^2$, R$^3$ and R$^4$ have the above meanings, with acids or reactive acid derivatives corresponding to formula III

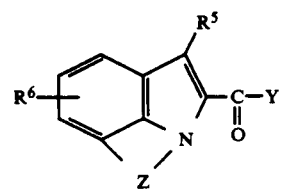

(III)

in which R$^5$, R$^6$ and Z have the above meanings, and Y represents hydroxyl or a reactive group, and, optionally, converting free compounds of formula I into the acid addition salts thereof, or converting the acid addition salts into the free compounds of formula I.

The acylation of the amino compounds of formula II can be carried out by customary methods for the formation of amide groups by aminoacylation. Acylating agents which may be used include acids of formula IIIa

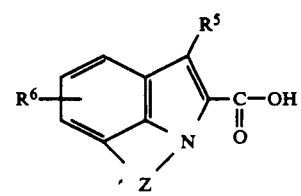

(IIIa)

in which R$^6$, R$^7$ and Z have the above meanings, or the reactive derivatives thereof. Particularly suitable reactive derivatives are mixed anhydrides, esters and acid halides. Thus, reactive groups Y can represent, for example, lower alkoxy, halogens such as chlorine or bromine or, preferably, organic sulfonic acid residues, for example residues of lower alkanesulfonic acids such as, for example, methanesulfonic acid or of aromatic sulfonic acids such as benzenesulfonic acid, or benzenesulfonic acids substituted by lower alkyl or halogen, for example toluenesulfonic acids or bromobenzenesulfonic acids. The acylation can be carried out in an organic solvent which is inert under the reaction conditions, preferably at temperatures between −20° C. and room temperature. Particularly suitable solvents include halogenated hydrocarbons such as dichloromethane or aromatic hydrocarbons such as benzene or toluene or cyclic ethers such as tetrahydrofuran or dioxane or mixtures of these solvents.

The acylation can advantageously be carried out, especially when a mixed anhydride of the acids of formula IIIa with a sulfonic acid is used as acylating agent, in the presence of an acid-binding reagent. Suitable acid-binding agents are bases soluble in the reaction mixture, especially organic bases such as tert.-lower alkylamines and pyridines such as, for example, triethylamine, tripropylamine, pyridine, 4-dimethylaminopyridine, 4-diethylaminopyridine or 4-pyrrolidinopyridine. It is also possible for organic bases employed in excess to act simultaneously as a solvent.

It is possible and advantageous for mixed anhydrides of the acids of formula IIIa with organic sulfonic acids to be obtained in situ by reacting the acids IIIa with an acid halide, especially the acid chloride of the organic sulfonic acid, and, without isolation, immediately further reacting with the amino compound of formula II.

If the acid itself, or an ester, is employed as acylating agent, the reaction of the amino compound of formula II with the acid of formula IIIa or the ester thereof may also advantageously be carried out in the presence of a coupling reagent known from peptide chemistry as suitable for amide formation. Examples of coupling reagents which promote amide formation with the free acids by reacting with the acid in situ to form a reactive acid derivative, include, in particular, alkylcarbodiimides, for instance, cycloalkylcarbodiimides such as dicyclohexylcarbodiimide, or 1-ethyl-3-[3-(dimethylamino)-propyl]-carbodiimide, carbonyldiimidazole and N-lower-alkyl-2-halopyridinium salts, especially halides or tosylates, preferably N-methyl-2-chloropyridinium iodide (see, for example, Mukaiyama in Angew. Chemie 91 789–812). The reaction in the presence of a coupling reagent can advantageously be carried out at temperatures from −30° C. to +50° C. using solvents such as halogenated hydrocarbons and/or aromatic solvents, optionally in the presence of an acid-binding amine.

The compounds of formula I can be isolated from the reaction mixture by known techniques and purified in a known manner. Acid addition salts can be converted in a customary manner into the free bases, and the latter can, if desired, be converted in a known manner into pharmaceutically acceptable acid addition salts. Examples of suitable pharmaceutically acceptable acid addition salts of the compounds of formula I include the salts thereof with inorganic acids, for example hydrogen halide acids, particularly hydrochloric acid, sulfuric acid or phosphoric acids or with organic acids, for example lower aliphatic mono- or dicarboxylic acids such as lactic acid, maleic acid, fumaric acid, tartaric acid or acetic acid or sulfonic acids, for example lower alkylsulfonic acids such as methanesulfonic acid or benzenesulfonic acids which are optionally substituted in the benzene ring by halogen or lower alkyl, such as p-toluenesulfonic acid or cyclohexylaminosulfonic acid.

If racemates of the compounds of formula II are employed in the synthesis, the compounds of formula I are obtained in the form of racemates. It is possible to obtain optically active compounds of formula I starting from optically active forms of the compounds of formula II. The optically active compounds of formula I can be obtained from the racemic mixtures in a known manner, for example by separation by chromatography on chiral separating materials or by reaction with suitable optically active acids, such as tartaric acid or 10-camphorsulfonic acid, and subsequent fractionation into the optically active antipodes thereof by fractional crystallization of the resulting salts.

The amine compounds of formula II are known or can be prepared by known processes or analogously to known processes. Thus, the amine compounds of formula II can be obtained, for example, in a known manner by reducing an oxime compound corresponding to formula IV

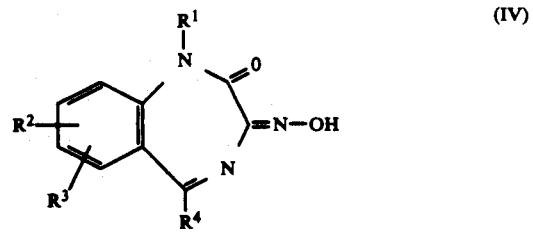

in which and $R^1$, $R^2$, $R^3$ and $R^4$ have the above meanings. The oximes of formula IV can be reduced to the amines of formula II by customary methods, for example catalytic hydrogenation, preferably in the presence of a Raney nickel catalyst or with zinc/glacial acetic acid as reducing agent. It may prove advantageous in the reduction with zinc/glacial acetic acid to add a halogenated organic carboxylic acid to activate the zinc.

The compounds of formula II contain an asymmetric carbon atom in the 3-position of the benzodiazepine structure. They are obtained in the form of racemates in the synthesis. The optically active compounds can be obtained from the racemic mixtures in a known manner, for example by chromatographic separation on chiral separating materials or by reaction with suitable optically active acids, for example tartaric acid or 10-camphorsulfonic acid, and subsequent fractionation into the optically active antipodes thereof by fractional crystallization of the resulting salts. Racemic mixtures of the amines of formula II can, for the fractionation, also first be reacted with an optically active amino acid, for example phenylalanine, by methods customary in peptide chemistry to give the corresponding amides of the optically active amino acid. Thus, the racemic compounds of formula II can, for example, be reacted with an amino acid whose $NH_2$ group is protected by a protective group known from peptide chemistry, for example tert-.butoxycarbonyl (=BOC group), and the protective group can subsequently be eliminated again in a known manner. The pair of diastereomeric amides produced thereby can be fractionated in a known manner, for example by fractional crystallization or chromatography, and subsequently the amino compound of formula II can be liberated again from the amides in a known manner.

The oxime compounds of formula IV can be prepared in a known manner by nitrosation of compounds of formula V

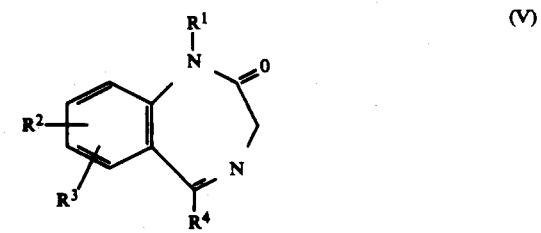

in which $R^1$, $R^2$, $R^3$, and $R^4$ have the above meaning. It is advantageous for the compounds of formula V which are unsubstituted in the 3-position first to be treated with a strong base, for example an alkali metal alcoholate such as potassium tert.butylate, in an organic solvent which is inert under the reaction conditions, for example an aromatic hydrocarbon such as benzene or toluene or a cyclic ether such as tetrahydrofuran, and then reacted with a nitrosating agent, for example with a lower alkyl nitrite such as isoamyl nitrite or tert.butyl nitrite.

Compounds corresponding to the formula Va

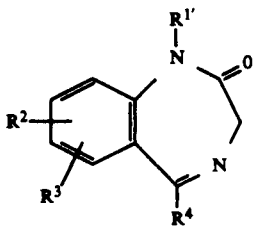

in which $R^{1'}$ has the meaning given for $R^1$ with the exception of hydrogen, and $R^2$, $R^3$ and $R^4$ have the above meaning, can be obtained in a known manner by oxidizing 2-chloromethyl-1,4-benzodiazepine compounds corresponding to the formula VI

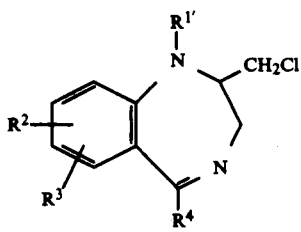

in which $R^{1'}$, $R^2$, $R^3$ and $R^4$ have the above meanings, in a known manner known. The oxidation can be carried out, for example, by treating the compounds of the formula VI with a suitable oxidizing agent in the presence of a solvent which is inert under the reaction conditions. Examples of oxidizing agents which can be employed include potassium permanganate, chromium trioxide or dichromate salts. Examples of suitable solvents which are inert to these oxidizing agents include halogenated hydrocarbons such as dichloromethane, water or acetic acid, or mixtures thereof.

The starting compounds of formula VI are known or can be prepared by known methods or analogously to known methods.

The compounds can be obtained, for example, in a known manner by the methods described in German published application Nos. DE 22 21 558 or DE 25 20 937 starting from 2-hydroxy-1,3-diaminopropane compounds corresponding to the formula VIII

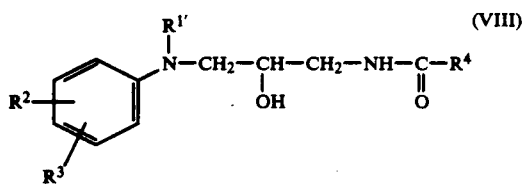

in which $R^{1'}$, $R^2$, $R^3$ and $R^4$ have the above meanings. The compounds of formula VIII are cyclized by treatment with phosphorus oxychloride. For this purpose, the compounds of formula VIII or the acid addition salts thereof are advantageously treated with phosphorus oxychloride at a temperature between 100° and 150° C., preferably at the boiling point of the reaction mixture. This results in a mixture of a 2-chloromethyl-1,4-benzodiazepine compound of formula VI with the 3-chloro-1,5-benzodiazocine compound of formula VII, which is isomeric thereto,

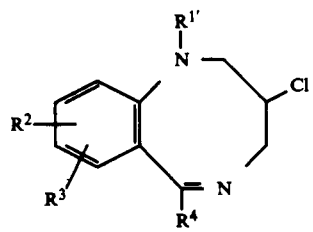

in which $R^{1'}$, $R^2$, $R^3$ and $R^4$ have the above meanings. The benzodiazocine compound of formula VII in the mixture can be rearranged into the isomeric compound of formula VI in a known manner, for example by heating the mixture in an organic solvent which is inert under the reaction conditions, for example a high-boiling halogenated hydrocarbon such as tetrachloroethane.

Preparation of 2-hydroxy-1,3-diaminopropane compounds of formula VIII can start from anilines of formula IX

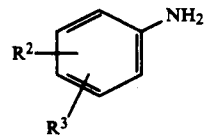

in which $R^2$ and $R^3$ have the above meanings. The amino group in these anilines is first monosubstituted by an $R^{1'}$ group in a known manner and subsequently reacted analogously to the method described in German published application No. DE 28 10 349 with 1,2-epoxypropylphthalimide, or first with epichlorohydrin and thereafter with phthalimide. The phthalimide group is subsequently cleaved in a known manner, and the resulting compounds of formula X

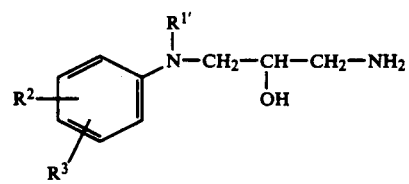

in which $R^{1'}$, $R^2$ and $R^3$ have the above meaning, are acylated with acid halides corresponding to the formula XI $R^4$—CO—Cl  (XI)

in which $R^4$ has the above meaning.

Compounds of formula V can also be obtained starting from ketones corresponding to the formula XII

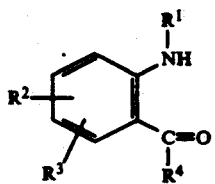

(XII)

in which $R^1$, $R^2$, $R^3$ and $R^4$ have the above meanings, in a known manner, by reacting a ketone of formula XII with a haloacetyl halide to give a compound corresponding to the formula XII

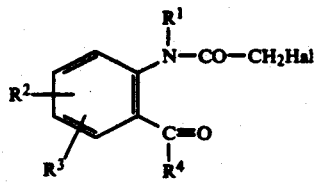

(XIII)

in which $R^1$, $R^2$, $R^3$ and $R^4$ have the above meanings, and Hal represents chlorine or bromine, and subsequently condensing the compound of formula XIII with ammonia to give a compound of formula V.

The ketones of formula XII are known or can be prepared by known methods or analogously to known methods, for example by reaction of p-substituted anilines corresponding to formula IX with acid halides of formula XI, for example in a Friedel Crafts reaction with subsequent hydrolysis, or starting from anthranilic acids, by first condensing the acid with acetic anhydride, reacting the condensation product in a Grignard reaction with a compound corresponding to the formula XIV

 $R^4—MgBr$ (XIV)

in which $R^4$ has the above meaning, to give the N-acetyl derivatives of the compounds of formula XII, and hydrolyzing the latter.

Compounds corresponding to the formula V in which $R^1$ represents hydrogen can be alkylated in a known manner to give other compounds of formula V, for example by reaction with a compound corresponding to the formula XV

 $R^{1'}—Hal$ (XV)

in which $R^{1'}$ has the above meaning, and Hal represents chlorine, bromine or iodine.

The esters of formula IIIb

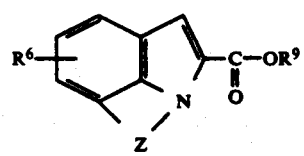

(IIIb)

in which $R^6$ and Z have the above meanings, and $R^9$ represents lower alkyl, can be obtained in a known manner starting from compounds corresponding to the formula XVI

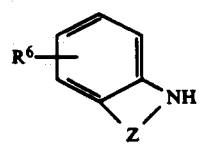

(XVI)

in which $R^6$ and Z have the above meanings, by treating a compound of formula XVI with sodium nitrite to convert it into the corresponding N-nitroso compound, and reducing the nitroso compound to a hydrazine compound corresponding to the formula XVII

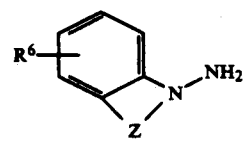

(XVII)

in which $R^6$ and Z have the above meanings, and reacting the hydrazine compound of formula XVII further with a lower alkyl pyruvate corresponding to the formula XVIII

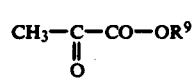

(XVIII)

in which $R^9$ has the above meaning, in a known manner under the conditions of the Fischer indole synthesis, so that a hydrazone compound corresponding to the formula XIX

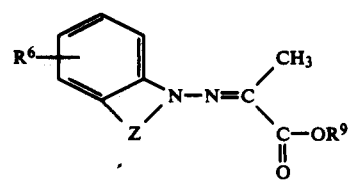

(XIX)

in which $R^6$, $R^9$ and Z have the above meanings, is formed as an intermediate which condenses further to give an ester of formula IIIb. Examples of reducing agents which can be used to reduce the nitroso compounds include lithium aluminum hydride in tetrahydrofuran or metallic zinc powder in the presence of acid. Catalytic hydrogenation of the nitroso compounds to the hydrazines of formula XVII is also possible. It is possible and advantageous to prepare the esters of formula IIIb starting from compounds of formula XVI in a one-pot process without isolating the individual intermediates. This entails adding hydrochloric acid to the reaction mixture containing zinc salts and the hydrazine compound of formula XVII obtained after reducing the N-nitroso compound, to further acidify the mixture, and then adding the pyruvic ester of formula XVIII to the reaction mixture. Upon addition of the pyruvic ester of formula XVIII to the reaction mixture, the hydrazone compound of formula XIX is formed as an intermediate which further condenses under the reaction conditions to give the ester of formula IIIb.

It is possible to hydrolyze the esters of formula IIIb in a known manner to the corresponding acids and/or to convert the esters into reactive acid derivatives of such acids.

Upon conversion into an acid halide, a halogen substituent $R^5$ is also introduced into the compounds at the same time.

The 1,7-fused 1H-indole-2-carboxylic acid-N-(1,4-benzodiazepin-3-yl)amide derivatives according to the invention and the pharmacologically acceptable acid addition salts thereof have valuable pharmacological properties, in particular CCK-antagonistic effects and are distinguished by a novel, favorable activity profile. Thus, the compounds of formula I having CCK-antagonizing activity according to the invention exhibit a pronounced activity of promoting emptying of the stomach as well as inhibitory influences on CCK-induced exocrine pancreas secretion. In the dose range effective to promote emptying of the stomach, they only exhibit to a slight extent the side effect of inhibiting gallbladder contraction and are distinguished by a low toxicity and a large therapeutic index. Due to their favorable activity profile, the compounds are suitable for treating CCK-related disturbances of the emptying of the stomach.

CCK comprises peptides of various chain lengths and acts as a hormone and as a neuropeptide. Among the CCK peptides, the octapeptide CCK-8 is the smallest unit with the complete spectrum of CCK effects. Therefore, the following pharmacological tests were performed with CCK-8.

DESCRIPTION OF PHARMACOLOGICAL TEST METHODS

1. Determination of the peripheral CCK receptor binding affinity of the test substances.

The affinity of the compounds of formula I for peripheral CCK receptors was measured in vitro on rat pancreas homogenate. The inhibition of the binding of the physiologically relevant octopeptide CCK-8 to peripheral CCK receptors by the test substances was determined.

The receptor binding studies were carried out by a modification of the method of van Dijk et al. (J. Neuroscience 4 (1984), 1021-1033), using soya bean trypsin inhibitor (=SBTI) as protease inhibitor. $^3$[H]-CCK-8, code TRK 775, from Amersham Int., having a specific activity of 60-90 Ci/mmol, was used as tritium-labelled CCK-8.

Whole pancreas glands from male Wistar rats with a body weight of 150-300 g, which had been sacrificed by decapitation, were freed of fatty tissue and homogenized for 15 seconds in a 50-fold volume of an ice-cold test buffer solution (10 mmol 2-[4-(2-hydroxyethyl)-piperazin-1-yl]-ethanesulfonic acid (=HEPES), 130 mmol sodium chloride, 5 mmol magnesium chloride, 0.02% bacitracins, 0.01% SBTI, pH 7.4) with a Kinematica Polytron type homogenizer. The homogenates were then centrifuged at 48,000 g for 10 minutes. This washing method was repeated. After the last centrifugation, the residue which was obtained each time in the form of a pellet was suspended in a 550-fold volume of the test buffer solution and immediately used for the measurement.

For the binding test, 500 μl of the tissue homogenate were incubated with 50 μl of test buffer solution or 50 μl of a solution of the compound to be investigated and with 50 μl of a $^3$[H]-CCK-8 solution (final concentration 0.3 nM). The non-specific binding was assumed to be 0.1 μmol CCK-8. The incubation lasted 90 minutes at 25° C. All the compounds were measured 3 times at each of several concentrations.

Aqueous solutions were employed as test substance solutions and were prepared by appropriate dilution of $60\times10^{-4}$ molar aqueous stock solutions. Test substances which are sparingly soluble in water were first dissolved in 96% ethanol, and this solution was diluted with sufficient water for the ethanol concentration not to exceed 1.6% by volume in the solution to be tested.

Bound and free $^3$[H]-CCK-8 were separated by filtration through glass fiber filters. The filters were washed twice with 3 ml of HEPES solution each time and then placed in the scintillation solution (SAVE scintillation solution from Packard) in the dark overnight and counted in a Packard TriCarb 1500 TM liquid scintillation counter. The $IC_{50}$ of the respective test substance was determined to be that concentration which caused a 50% inhibition of the specific binding of tritiated CCK-8 to the receptors. From this, the corresponding pKi value was calculated using the Cheng-Prusoff equation.

The following Table A shows the pKi values for the affinity of the test substances for peripheral CCK receptors obtained by the test method described above. The example numbers listed for the compounds of formula I refer to the following preparative examples.

2. Determination of the minimum toxic dose.

Male mice weighing 20-25 g were given maximum oral doses of 300 mg/kg of the test substance. The animals were observed carefully for three hours for symptoms of toxicity. In addition, all symptoms and deaths were recorded for a period of 24 hours after administration. Concomitant symptoms were likewise observed and recorded. If death or serious symptoms of toxicity were observed, further mice were given increasingly lower doses. The lowest dose which caused death or serious symptoms of toxicity is indicated in the following Table A as the minimum toxic dose.

TABLE A

| Ex. No. | In vitro binding to peripheral CCK receptors (pancreas) pKi values | Minimum toxic dose mg/kg mouse oral |
|---|---|---|
| 1 | 8.87 | >300 |
| 2a | 9.59 | |
| 2b | 7.71 | |
| 4 | 8.60 | >300 |
| 5 | 8.84 | >300 |
| 6 | 8.49 | |
| 8 | 8.04 | |
| 9 | 9.10 | >300 |
| 10 | 8.75 | 300 |
| 11 | 8.62 | 300 |
| 13 | 9.00 | >300 |
| 15 | 8.91 | |
| 17 | 8.00 | |
| 18 | 8.93 | >300 |
| 20 | 9.07 | >300 |
| 22 | 9.04 | >300 |
| 23 | 8.00 | >300 |
| 25 | 7.62 | >300 |
| 26 | 8.21 | |
| 30 | 8.63 | 300 |
| 33 | 8.43 | >300 |
| 37 | 9.19 | |
| 38 | 9.01 | |

3. Investigation of the effect of the test substances on CCK-induced disturbances of emptying of the stomach.

Doses of CCK lead to substantial blockade of the transpyloric transport of chyme from the stomach into the duodenum. The ability of the test substances to eliminate this blocking effect of CCK was investigated.

Female NMRI mice having body weights of 20-25 g were used in groups of ten animals each. After withdrawal of feed for 24 hours (drinking water ad libitum) the animals were given an oral dose of the test substance suspended in a volume of 10 ml/kg of body weight of a 1% strength Tylose ® solution (=methylcellulose) or in a volume of 10 ml/kg of body weight of a solubilizer solution which contains 5% glycerol, 87% polyethylene glycol 400, and 8% water. A control group received only the Tylose ® solution or the solution containing the solubilizer polyethylene glycol in each case. 60 minutes later the animals were given a subcutaneous injection of 80 Ig/kg CCK-8. After a further 5 minutes the animals were each orally administered 0.3 ml of a charcoal suspension (5% charcoal in 2% strength Tylose solution). The mice were sacrificed 5 minutes later and subsequently dissected. They were examined to find whether charcoal suspension had advanced into the duodenum.

Whereas under control conditions, i.e. without a dose of CCK, charcoal suspension was found in the duodenum of all the mice, transport of the chyme into the duodenum was prevented in the groups of control animals which received a dose of CCK, and traces of charcoal suspension were found in the duodenum of not more than 5% of the animals. The percentage of animals in which the CCK effect was eliminated and charcoal suspension was found in the duodenum after administration of the test substances was determined.

The following Table B lists the results obtained in the foregoing tests for dosages of the test substances which inhibit the CCK effect in at least 40% of the animals. It is evident from the table that the activity of the substances can often be considerably enhanced by administration in a solution containing PEG 400 solubilizer.

TABLE B

| Ex. No. | CCK-antagonistic Effect on CCK-induced Disturbance of Stomach Emptying | |
|---|---|---|
| | Dose μmol/kg Mouse oral | % of Animals in which the CCK Effect was Eliminated |
| 1 | 0.215 | 50 |
| 2a | 0.1 | 100 |
| 2b | 10 | 70 |
| 4 | 1.0 | 45 |
| 5 | 10 | 75 |
| 6 | 0.681 | 40 |
| 9 | 0.215 | 50 |
| 10 | 0.1 | 40 |
| 13 | 10 | 83 |
| | 1.0* | 100 |
| 15 | 1.0 | 57 |
| | 0.10* | 90 |
| 17 | 1.0* | 50 |
| 20 | 1.0 | 50 |
| 27 | 1.0 | 40 |
| 33 | 1.0 | 50 |

* = administered in solution containing solubilizer.

4. Determining the inhibitory effect of Test Substances on CCK-Induced Gallbladder Emptying.

CCK causes a contraction of the muscles of the gallbladder and thus an emptying of the gallbladder. This results in the weight of the gallbladder decreasing compared with control animals not treated with CCK. Intraperitoneal doses of 0.1 μg/kg CCK-8 may result in the weight of the gallbladders decreasing to about 1/10 of the original weight.

Female NMRI mice having a body weights of 20-25 g were used in groups of 10 animals each. After withdrawal of feed for 24 hours (drinking water ad libitum) the animals received an oral dose of the test substance suspended in a volume of 10 ml/kg of body weight of a 1% strength Tylose ® solution (=methylcellulose) or in a volume of 10 ml/kg of body weight of a solubilizer solution which contained 5% glycerol, 87% polyethylene glycol 400, and 8% water. Two control groups each received only the Tylose ® solution or the solution containing the solubilizer polyethylene glycol. One of the control groups and all the animals treated with test substance received 0.1 Ig/kg CCK-8 injected i.p. 60 minutes later.

The mice were sacrificed 5 minutes after the CCK-8 administration, and the gallbladders were excised and weighed.

The following Table C lists the percentage inhibition of the CCK-8 effect on gallbladder weights caused by the test substances.

TABLE C

| Ex. No. | CCK-Antagonistic Effect on the Gallbladder | |
|---|---|---|
| | Dose μmol/kg Mouse oral | % Inhibition of CCK-induced Gallbladder Emptying |
| 1 | 10 | 66 |
| | 1 | <25 |
| 2a | 0.46 | 16 |
| 2b | 46 | 8.3 |
| 6 | 10 | 73 |
| 9 | 100 | 99 |
| | 4.6 | <25 |
| 15 | 100 | 100 |
| | 10 | <25 |
| | 0.1* | <25 |
| 20 | 10 | 25 |
| 33 | 10 | 19 |

Comparison of the data in Tables B and C shows that CCK-antagonistic effects on the gallbladder were not observed until the doses of substances were a multiple of the dosage ranges effective to prevent CCK-induced disturbances of stomach emptying.

The doses to be used may vary between individuals and, naturally, vary depending on the type of condition to be treated, the substance used and the form of administration. For example, parenteral formulations will generally contain less active substance than oral products. However, drug forms with an active substance content of 5-50 mg per single dose are generally suitable for administration to larger mammals, in particular humans.

Pharmaceutical compositions may contain the compounds of formula I or physiologically acceptable acid addition salts thereof together with conventional pharmaceutical adjuvants in pharmaceutical forms such as, for example, tablets, capsules, suppositories or solutions. The compounds of formula I are distinguished by being readily soluble in solutions containing customary pharmaceutical adjuvants and by being highly absorbable. The pharmaceutical formulations can be prepared by known methods using customary solid vehicles such as, for example, lactose, starch or talc or liquid diluents such as, for example, water, fatty oils or liquid paraffins and using conventional pharmaceutical adjuvants, for example tablet disintegrating agents or preservatives.

The following examples are intended to illustrate the invention in further detail without limiting its scope in any way.

EXAMPLE 1

3-[(4H-Pyrrolo[3,2,1-ij]-5,6-dihydroquinoline-2-carbonyl)-amino]-8-methoxy-1-methyl-2-oxo-5-phenyl-1H-2,3-dihydro-1,4-benzodiazepine.

(A) 43 g of $N_1$-methyl-$N_1$-(3-methoxyphenyl)-2-hydroxy-1,3-diaminopropane and 31 ml of triethylamine were dissolved in 280 ml of dichloromethane. While cooling in ice, a solution of 24.4 ml of benzoyl chloride in 20 ml of dichloromethane was slowly added dropwise to the solution. The reaction mixture was stirred at room temperature for 1.5 hours. The reaction solution was subsequently worked up by washing with water and sodium chloride solution and evaporating the solvent. The remaining residue was 70.0 g of crude $N_1$-methyl-$N_1$-(3-methoxyphenyl)-$N_2$-benzoyl-2-hydroxy-1,3-diaminopropane. The pure product obtained by recrystallization from toluene/isopropanol had a melting point of 87-89° C.

(B) 64 g of the product obtained above were reacted with 64 ml of phosphorus oxychloride in an oil bath at a bath temperature of 130° C. for 1.5 hours. The mixture was then cooled and diluted with dichloromethane, and ice-water was added to the solution. The organic phase was separated, washed several times with water and then treated with dilute sodium hydroxide solution, washed again with water, dried over sodium sulfate, and evaporated. The residue obtained was 56.7 g of an oily crude product which contained a mixture of about 60% 2-chloromethyl-1-methyl-8-methoxy-5-phenyl-2,3-dihydro-1H-1,4-benzodiazepine and about 40% 3-chloro-1-methyl-9-methoxy-6-phenyl-1,2,3,4-tetrahydro-1,5-benzodiazocine. To isomerize the benzodiazocine fraction, the crude mixture was heated in 222 ml of tetrachloroethane under reflux for 30 minutes. The tetrachloroethane was subsequently evaporated, and the remaining 2-chloromethyl-1-methyl-8-methoxy-5-phenyl-2,3-dihydro-1H-1,4-benzodiazepine was further processed in the next reaction stage without purification.

(C) 56.7 g of the product obtained above were dissolved in 285 ml of dichloromethane. To the solution were added 322 ml of 32% strength aqueous hydrochloric acid, 2481 ml of water and 255 ml of dichloromethane. A solution of 32.4 g of potassium permanganate in 660 ml of water was subsequently added dropwise, maintaining the internal temperature below 15° C. by cooling in ice. The reaction mixture was then stirred at room temperature for half an hour. The reaction mixture was worked up by adding solid sodium bicarbonate in portions until the reaction mixture was neutral, filtering out the precipitate which formed from the solution through asbestos slurry (commercial product Theorit ®) with suction, separating the dichloromethane phase, and extracting the aqueous phase again with dichloromethane. The combined dichloromethane extracts were washed with dilute sodium hydroxide solution and then with water, dried over magnesium sulfate and evaporated. 55 g of crude product were obtained. The crude product was subjected to column chromatography on silica gel under slightly elevated pressure (flash chromatography) using cyclohexane/ethyl acetate 4:6 as the eluent to isolate pure 1-methyl-8-methoxy-2-oxo-5-phenyl-2,3-dihydro-1H-1,4-benzodiazepine. 15.5 g of oily pure product were obtained.

(D) 15.5 g of the above product were suspended in 293 ml of toluene. The suspension was cooled to −20° C. and then 16.4 g of potassium tert.-butylate were added, while stirring, and the mixture was stirred for a further 15 minutes. Then 9.4 ml of isoamyl nitrite were added, while cooling, at such a rate that the temperature of the reaction mixture remained below 0° C. It was then stirred at 0° C. for 30 minutes. The reaction mixture was then worked up by stirring it into a mixture of 586 ml of ice-cold water, 29 ml of glacial acetic acid and 586 ml of ethyl acetate. After vigorous mixing the organic phase was separated and the aqueous phase was extracted once more with ethyl acetate. The combined organic phases were washed with water and evaporated. 21 g of crude product were obtained. This was crystallized from toluene/ethanol. The crystals were separated out, and the mother liquor was again purified by flash chromatography on 100 g of silica gel using cyclohexane/ethyl acetate 4:6 as the eluent and evaporated. The residue was crystallized from ethanol and combined with the aforementioned crystals. A total of 9.5 g of 3-hydroxyimino-1-methyl-8-methoxy-2-oxo-5-phenyl-2,3-dihydro-1H-1,4-benzodiazepine having a melting point of 206-207° C. was obtained.

(E) 9.5 g of the product obtained above were added to a mixture of 700 ml of glacial acetic acid and 80 ml of trifluoroacetic acid. The reaction mixture was heated to 40° C. (internal temperature) and a total of 6.9 g of zinc dust was added in portions while stirring, the mixture was stirred at 40° C. for a further 2 hours and then 1 g of zinc dust was again added and the mixture was stirred at 40° C. for a further 1.5 hours. The mixture was worked up by diluting with toluene, allowing it to cool and evaporating the solvent. The remaining residue was taken up in dichloromethane, and the solution was washed with aqueous sodium carbonate solution and water. Solids were filtered out with suction through Theorit ®, and the solution was dried and evaporated. 8.1 g of crude 3-amino-1-methyl-8-methoxy-2-oxo-5-phenyl-2,3-dihydro-1H-1,4-benzodiazepine were obtained and were further reacted in the subsequent reaction stage H without purification.

(F) 150 g of 1,2,3,4-tetrahydroquinoline were dissolved in 1.25 l of glacial acetic acid. A solution of 80 g of sodium nitrite in 300 ml of water was added to the solution while cooling in an ice bath to an internal temperature of about 15° C., and the reaction mixture was stirred for a further 45 minutes. 300 g of zinc dust were added in portions over the course of 1.5 hours to the reaction solution which contained the N-nitroso-1,2,3,4-tetrahydroquinoline formed, during which the reaction mixture was maintained at an internal temperature of 15-20° C. by cooling in an ice bath. Subsequently 1.75 l of water and 1.25 l of 32% strength aqueous hydrochloric acid were added to the mixture, which was stirred for a further 1.5 hours. 130 g of ethyl pyruvate were added to the acidic reaction mixture which contained the resulting N-amino-1,2,3,4-tetrahydroquinoline and the zinc salt, and the mixture was heated to reflux for 1.5 hours and subsequently allowed to stand for a further 16 hours. This involved in situ condensation of the hydrazone formed as an intermediate to give ethyl 4H-pyrrolo[3,2,1-ij]-5,6-dihydroquinoline-2-carboxylate.

The reaction mixture was worked up by extracting twice with a total of 5 l of dichloromethane, and the dichloromethane extracts were combined, washed twice with a total of 1 l of water, dried over sodium sulfate and reduced in volume. 280 g of crude ethyl 4H-pyrrolo[3,2,1-ij]-5,6-dihydroquinoline-2-carboxylate were obtained and were purified by chromatography on silica gel using dichloromethane as the eluent. 151.8 g of purified product having a melting point of 70-72° C. were obtained.

(G) 39 g of ethyl 4H-pyrrolo[3,2,1-ij]-5,6-dihydroquinoline-2-carboxylate were dissolved in 40 ml of ethanol, and this solution was added at room temperature to a solution of 11.3 g of potassium hydroxide in a mixture of 20 ml of water and 145 ml of ethanol. The reaction mixture was stirred at room temperature for 90 minutes and then cooled to 10° C. The precipitated solid was filtered out with suction and washed three times with 30 ml of ethanol each time. The mother liquor was reduced to half volume, and the solid which thereby precipitated was likewise separated out and washed with ethanol.

All the solid was then dissolved in 150 ml of water, and the acid was precipitated by acidifying the solution with concentrated hydrochloric acid to pH 1 to 2. The precipitated acid was separated out, washed three times with 40 ml of water each time and dried at 60° C. 32.4 g of 4H-pyrrolo[3,2,1 -ij]-5,6-dihydroquinoline-2-carboxylic acid having a melting point of 212-213° C. (decomposition) were obtained.

(H) 5.4 g of 4H-pyrrolo[3,2,1-ij]-5,6-dihydroquinoline-2-carboxylic acid and 3.67 ml of triethylamine were dissolved in 119 ml of dichloromethane. The solution was cooled to −20° C. and, while stirring, 2.08 ml of methanesulfonyl chloride were slowly added dropwise, and the reaction mixture was stirred at −20° C. for a further 15 minutes. To the reaction solution containing the mixed anhydride from methanesulfonic acid and 4H-pyrrolo[3,2,1-ij]-5,6-dihydroquinoline-2-carboxylic acid was added dropwise, while stirring, a solution of 8 g of 3-amino-1-methyl-8-methoxy-2-oxo-5-phenyl-2,3-dihydro-1H-1,4-benzodiazepine obtained in stage E and 3.67 ml of triethylamine in 100 ml of dichloromethane at a temperature between −15° and −20° C., and the reaction mixture was stirred at −15° C. for a further 30 minutes and allowed to warm slowly (within one hour) to room temperature. The reaction mixture was worked up by diluting with water, separating the dichloromethane phase, washing the dichloromethane phase with sodium bicarbonate solution and then with water, drying over sodium sulfate, filtering and evaporating the solvent. 14.3 g of the crude title compound were obtained as a residue. The crude product was purified by column chromatography on 700 g of silica gel under slightly elevated pressure (flash chromatography) using cyclohexane/ethyl acetate 1:1 as the eluent. 6.1 g of purified product were obtained. This was crystallized from 25 ml of ethanol with addition of a small amount of dichloromethane, and the crystals were dried at 80° C. for 2 days. 3.3 g of racemic 3-[(4H-pyrrolo[3,2,1-ij ]-5,6-dihydroquinoline-2-carbonyl)-amino]-8-methoxy-1-methyl-2-oxo-5-phenyl-1H-2,3-dihydro-1,4-benzodiazepine having a melting point of 175-178° C. were obtained.

EXAMPLE 2

Preparation of the optical isomers of 3-[(4H-pyrrolo[3,2,1-ij ]-5,6-dihydroquinoline-2-carbonyl)-amino]-8-methoxy-1-methyl-2-oxo-5-phenyl-1H-2,3-dihydro-1,4-benzodiazepine.

2a: (−) isomer, optical rotation $[\alpha]_D^{20} = -88.2°$ (c=0.5 in dichloromethane).

(A) 30.5 g of racemic 3-amino-1-methyl-8-methoxy-2-oxo-5-phenyl-2,3-dihydro-1H-1,4-benzodiazepine (prepared analogously to Example 1 E) were dissolved in 190 ml of dimethylformamide. To the solution were successively added, under exclusion of moisture, 28.8 g of N-tert.-butoxycarbonyl-D-phenylalanine (=BOC-D-phenylalanine), 15 g of 1-hydroxybenzotriazole, 20.7 g of 1-ethyl-3-[3-(dimethylamino)-propyl-carbodiimide hydrochloride and 15 ml of triethylamine. The reaction mixture was stirred at room temperature for 30 minutes. To work up the reaction mixture, the dimethylformamide was removed by distillation under reduced pressure, and the residue was dissolved in ethyl acetate. The solution was shaken with 10% strength aqueous citric acid solution, the phases were separated from one another, the aqueous phase was extracted once more with ethyl acetate, and then the combined organic phases were washed with 10% strength aqueous sodium hydroxide solution, water and aqueous sodium chloride solution, dried over sodium sulfate and filtered. Removal of the solvent by distillation resulted in 66 g of crude product which was purified again by flash chromatography on 700 g of silica gel using cyclohexane/ethyl acetate 1:1 as the eluent. After evaporation of the solvent, 60 g of 1,1-dimethylethyl-N-((R)-2-[(2,3-dihydro-1-methyl-2-oxo-5-phenyl-8-methoxy-1H-1,4-benzodiazepin-3-yl)amino]-2-oxo-1-benzylethyl)-carbamate were obtained as a 1:1 mixture of diastereomers.

(B) 60 g of the mixture of diastereomeric amides obtained above were dissolved in 480 ml of ethyl acetate. To eliminate the BOC protective group from the amides, the solution was saturated with gaseous hydrogen chloride, and the reaction mixture was stirred for 30 minutes. This resulted in crystals of the hydrochloride of the liberated amines in which the diastereomer with (−)-rotation was enriched. The crystals were filtered out with suction. Three recrystallizations from ethanol yielded a diastereomerically pure hydrochloride of 3-phenyl-2-amino-N-(2,3-dihydro-1-methyl-2-oxo-5-phenyl-8-methoxy-1H-1,4-benzodiazepin-3-yl)-propionamide with (−)-rotation in dichloromethane solution. To liberate the base, 10% strength sodium hydroxide solution was added to the hydrochloride, and the base was extracted from the aqueous phase with ethyl acetate. The organic phase was washed, dried and evaporated to result in 18.4 g of diastereomerically pure 3-phenyl-2-amino-N-(2,3-dihydro-1-methyl-2-oxo-5-phenyl-8-methoxy-1H-1,4-benzodiazepin-3-yl)propionamide. Rotation $[\alpha]_D^{20}$ of −30.6° (c=0.5 in dichloromethane).

(C) 18.4 g of the diastereomerically pure amide with (−)-rotation in dichloromethane solution obtained above were dissolved in 100 ml of dichloromethane. 5.4 ml of phenyl isothiocyanate were added to the solution under exclusion of moisture, and the reaction mixture was stirred at room temperature for 10 minutes. The dichloromethane was then removed by distillation under reduced pressure, and the remaining residue was purified by flash chromatography on 500 g of silica gel using cyclohexane/ethyl acetate 1:1 as the eluent. Evaporation of the solvent resulted in a resinous foam which was crystallized from ethanol. 20.1 g of N$_1$-phenyl-N$_2$-(2-[(2,3-dihydro-1-methyl-2-oxo-5-phenyl-8-methoxy-1H-1,4-benzodiazepin-3-yl)amino]-2-oxo-1-(benzyl)-ethyl)-thiourea having a melting point of 138–160° C. were obtained. Optical rotation: $[\alpha]_D^{20} = -11.2°$ (c=0.5 in methanol).

(D) 30.7 ml of trifluoroacetic acid were added to 20 g of the thiourea product obtained above, and the reaction mixture was heated at 50° C. for 20 minutes. The trifluoroacetic acid was then removed by distillation under reduced pressure, and the remaining residue was evaporated twice with dichloromethane, redissolved in dichloromethane and purified by flash chromatography on 500 g of silica gel, initially using as the eluent a 1:1 cyclohexane/ethyl acetate mixture and then a 90:10:1:1 mixture of dichloromethane/methanol/acetic acid/water. The resulting hydrotrifluoroacetate of (−)-3-amino-2,3-dihydro-1-methyl-2-oxo-5-phenyl-8-methoxy-1H-1,4-benzodiazepine was dissolved in dichloromethane, aqueous sodium bicarbonate solution was added to the solution to liberate the amine, and the reaction mixture was extracted with dichloromethane. The dichloromethane phase was separated, dried over sodium sulfate and filtered; the solvent was removed by distillation under reduced pressure, and the remaining base was dried. 8.5 g of (−)3-amino-2,3-dihydro-1-methyl-2-oxo-5-phenyl-8-methoxy-1H-1,4-benzodiazepine were obtained as a foam. Optical rotation $[\alpha]_D^{20} = -171.2°$ (c=0.5 in dichloromethane).

(E) In accordance with the method described in Example 1 H), 7.0 g of the (−)-3-amino-1-methyl-8-methoxy-2-oxo-5-phenyl-2,3-dihydro-1H-1,4-benzodiazepine obtained above were reacted with a reaction solution containing the mixed anhydride from 4.9 g of 4H-pyrrolo[3,2,1-ij]-5,6-dihydroquinoline-2-carboxylic acid and 1.85 ml of methanesulfonyl chloride in dichloromethane. The reaction mixture was worked up as described in Example 1 H). Purification by flash chromatography resulted in 9.0 g of purified crystalline product. This was recrystallized twice more from methanol and once from ethanol to remove any enantiomeric impurities. 6.7 g of enantiomerically pure (−)-3-[(4H-pyrrolo[3,2,1-ij]-5,6-dihydroquinoline-2-carbonyl)-amino]-8-methoxy-1-methyl-2-oxo-5-phenyl-1H-2,3-dihydro-1,4-benzodiazepine having a melting point of 201–205° C. and an optical rotation $[\alpha]_D^{20}$ of −88.2° (c=0.5 in dichloromethane) were obtained.

2 b: 3-[(4H-pyrrolo[3,2,1-ij]-5,6-dihydroquinoline-2-carbonyl)-amino]-8-methoxy-1-methyl-2-oxo-5-phenyl-1H-2,3-dihydro-1,4-benzodiazepine with (+)-rotation in dichloromethane.

(A) The mother liquors produced in the preparation of the diastereomerically pure hydrochloride under 2a (B) were evaporated to obtain the other diastereomeric hydrochloride. The precipitated hydrochloride was recrystallized four times from a mixture of acetonitrile and isopropyl acetate. From the hydrochloride were obtained, analogously to the method described above, 14.5 g of diastereomerically pure 3-phenyl-2-amino-N-(2,3-dihydro-1-methyl-2-oxo-5-phenyl-8-methoxy-1H-1,4-benzodiazepin-3-yl)-propionamide with (+)-rotation in methanolic solution, having an optical rotation $[\alpha]_D^{20} + 162.6°$ (c=0.5 in methanol).

(B) 14.5 g of the amide with (+)-rotation in methanolic solution obtained above were reacted with 4.3 ml of phenyl isothiocyanate in dichloromethane analogously to Example 2a (C). The reaction mixture was worked up as described under Example 2a (C). 18.6 g of N$_1$-phenyl-N$_2$-{2-[(2,3-dihydro-1-methyl-2-oxo-5-phenyl-8-methoxy-1H-1,4-benzodiazepin-3-yl)-amino]-2-oxo-1-(benzyl)-ethyl}-thiourea were obtained. Optical rotation $[\alpha]_D^{20} = +60.2°$ (c=0.5 in methanol).

(C) 18.5 g of the thiourea product obtained above were reacted with 28.4 ml of trifluoroacetic acid analogously to Example 2a (D). The amine was liberated from the resulting hydrotrifluoroacetate of (+)-3-amino-2,3-dihydro-1-methyl-2-oxo-5-phenyl-8-methoxy-1H-1,4-benzodiazepine analogously to Example 2a (D). 7.7 g of (+)-3-amino-2,3-dihydro-1-methyl-2-oxo-5-phenyl-8-methoxy-1H-1,4-benzodiazepine were obtained. Optical rotation $[\alpha]_D^{20} = +143.8°$ (c=0.5 in dichloromethane).

(D) Analogously to the method described in Example 1 H), 5.0 g of the (+)-3-amino-1-methyl-8-methoxy-2-oxo-5-phenyl-2,3-dihydro-1H-1,4-benzodiazepine obtained above were reacted with a reaction solution containing the mixed anhydride from 3.49 g of 3-[(4H-pyrrolo[3,2,1-ij]-5,6-dihydroquinoline-2-carboxylic acid and 1.32 ml of methanesulfonyl chloride in dichloromethane. The reaction mixture was worked up as described in Example 1 H). 10 g of crude product were obtained. After purification by flash chromatography, three recrystallizations from methanol were carried out to remove any enantiomeric impurities. 3.4 g of enantiomerically pure (+)-3-[(4H-pyrrolo[3,2,1-ij]-5,6-dihydroquinoline-2-carbonyl)-amino]-8-methoxy-1-methyl-2-oxo-5-phenyl-1H-2,3-dihydro-1,4-benzodiazepine having a melting point of 201–205° C. were obtained. Optical rotation $[\alpha]_D^{20} = +88.4°$ (c=0.5 in dichloromethane).

EXAMPLE 3

3-[(4H-pyrrolo[3,2,1-ij]-5,6-dihydroquinoline-2-carbonyl)-amino]-1-n-pentyl-2-oxo-1H-2,3-dihydro-1,4-benzodiazepine.

(A) 10 g of 2-oxo-5-phenyl-2,3-dihydro-1H-1,4-benzodiazepine were dissolved in 100 ml of tetrahydrofuran under a nitrogen atmosphere. 1.4 g of sodium hydride in the form of an 80% oily suspension were added in portions to the solution under the nitrogen atmosphere, and the reaction mixture was heated to reflux for 30 minutes. 9.2 g (=5.5 ml) of iodopentane were slowly added dropwise, the mixture was heated to reflux for a further 1.5 hours and then another 0.3 g of sodium hydride in the form of an oily suspension was added and, after a further 10 minutes, another 5.5 ml of iodopentane were added dropwise, and the mixture was heated to reflux for a further hour. To work up the reaction mixture, ice-water was added to the reaction mixture and it was diluted with dichloromethane, the aqueous phase was separated, and the organic phase was washed to neutrality with water, dried over sodium sulfate, filtered and evaporated. 13.5 g of crude product were obtained and were purified by flash chromatography on about 300 g of silica gel using cyclohexane/ethyl acetate 1:1 as the eluent. The purified product was crystallized from cyclohexane and dried. 6.2 g of pure 2-oxo-1-n-pentyl-5-phenyl-2,3-dihydro-1H-1,4-benzodiazepine having a melting point of 93–95° C. were obtained.

(B) 6.5 g of the above product were suspended in 122 ml of toluene. The suspension was cooled to −20° C., and then 5.88 g of potassium tert.-butylate were added, while stirring, and the mixture was reacted with 2.84 ml of tert.-butyl nitrite as described in Example 1D. The reaction mixture was worked up as in Example 1D. This resulted in 4.7 g of 3-hydroxyimino-2-oxo-1-n-pentyl-5-phenyl-2,3-dihydro-1H-1,4-benzodiazepine having a melting point of 188–191° C.

(C) 4.6 g of the product obtained above were dissolved in a mixture of 328 ml glacial acetic acid and 37.6 ml trifluoroacetic acid and reduced with a total of 3.1 g of zinc dust as described in Example 1E. The reaction mixture was worked up as in Example 1E. 4.2 g of crude 3-amino-2-oxo-1-n-pentyl-5-phenyl-2,3-dihydro-1H-1,4-benzodiazepine were obtained and were further processed without purification.

(D) By the process described in Example 1H), a solution of 4.2 g of the product obtained above and 1.77 ml of triethylamine in 50 ml of dichloromethane was added dropwise at a temperature between −15° C. and −20° C. to a reaction solution containing the mixed anhydride from methanesulfonic acid and 2.6 g of 4H-pyrrolo[3,2,1-ij]-5,6-dihydroquinoline-2-carboxylic acid in 60 ml of dichloromethane. The reaction mixture was worked up as described in Example 1H). 3.9 g of 3-[(4H-pyrrolo[3,2,1-ij]-5,6-dihydroquinoline-2-carbonyl)-amino]-2-oxo-1-n-pentyl-5-phenyl-1H-2,3-dihydro-1,4-benzodiazepine were obtained as a white resinous foam. IR spectrum: 1682 cm$^{-1}$, 1662 cm$^{-1}$, 1524 cm$^{-1}$, 1499 cm$^{-1}$.

EXAMPLE 4

3-[(4H-pyrrolo[3,2,1-ij]-5,6-dihydroquinoline-2-carbonyl)-amino]-1-methyl-2-oxo-5-cyclohexyl-1H-2,3-dihydro-1,4-benzodiazepine.

(A) 75.6 g of $N_1$-methyl-$N_1$-phenyl-2-hydroxy-1,3-diaminopropane and 65 ml of triethylamine were dissolved in 600 ml of dichloromethane. The solution was cooled in ice while a solution of 61 ml of cyclohexylcarbonyl chloride in 50 ml of dichloromethane was slowly added dropwise. The reaction mixture was stirred at room temperature for 1.5 hours. The reaction solution was subsequently worked up by washing with water and with sodium chloride solution, and the solvent was evaporated. The remaining residue was 131 g of crude $N_1$-methyl-$N_1$-phenyl-$N_2$-cyclohexylcarbonyl-2-hydroxy-1,3-diaminopropane. The crude product was recrystallized from toluene, washed with ether and dried. 113.8 g of pure product having a melting point of 86–88° C. were obtained.

(B) 87 g of the product obtained above were reacted with 174 ml of phosphorus oxychloride in an oil bath at a bath temperature of 130° C. for 2 hours. The mixture was then cooled and diluted with dichloromethane, and ice-water was added to the solution. The organic phase was separated, washed several times with water, then treated with dilute sodium hydroxide solution, again washed with water, dried over sodium sulfate and evaporated. The residue obtained was 76.1 g of an oily crude product which contained a mixture of about 40% 2-chloromethyl-1-methyl-5-cyclohexyl-2,3-dihydro-1H-1,4-benzodiazepine and about 60% 3-chloro-1-methyl-6-cyclohexyl-1,2,3,4-tetrahydro-1,5-benzodiazocine. To isomerize the benzodiazocine fraction, the crude mixture was heated under reflux in 300 ml of tetrachloroethane for 30 minutes. The tetrachloroethane was then evaporated, and the remaining 2-chloromethyl-1-methyl-5-cyclohexyl-2,3-dihydro-1H-benzodiazepine was further processed without purification in the next reaction stage.

(C) 19.0 g of the product obtained above were dissolved in 103 ml of dichloromethane. 116 ml of 32% strength aqueous hydrochloric acid, 882 ml of water and 91 ml of dichloromethane were added to the solution. Subsequently a solution of 11.65 g of potassium permanganate in 238 ml of water was added dropwise, maintaining the internal temperature below 15° C. by cooling with ice. The reaction mixture was stirred at room temperature for 1.5 hours. Then another 2 g of potassium permanganate dissolved in 50 ml of water were added dropwise, and the mixture was stirred at room temperature for a further hour. To work up the reaction mixture, solid sodium bicarbonate was added in portions to the reaction mixture until neutrality. The dichloromethane phase was then separated, and the aqueous phase was again extracted with dichloromethane. The combined dichloromethane extracts were washed with dilute sodium hydroxide solution and then with water, dried over magnesium sulfate and evaporated. 55 g of crude product were obtained. The crude product was subjected to column chromatography on 1 kg of silica gel under slightly elevated pressure (flash chromatography) using cyclohexane/ethyl acetate 1:1 as the eluent to isolate pure 1-methyl-2-oxo-5-cyclohexyl-2,3-dihydro-1H-1,4-benzodiazepine, which was crystallized from ether and dried. 2.3 g of pure product having a melting point of 98–100° C. were obtained.

(D) 8.9 g of the above product were suspended in 201 ml of toluene. The suspension was cooled to −20° C. and then 9.63 g of potassium tert.-butylate were added while stirring, and the mixture was stirred for a further 15 minutes. Then 5.5 ml of isoamyl nitrite were added, while cooling, at such a rate that the temperature of the reaction mixture remained below 0° C. It was then stirred at 0° C. for 30 minutes. The reaction solution was then worked up by adding it to a stirred mixture of 347 ml of ice-cold water, 16.7 ml of glacial acetic acid, and 347 ml of ethyl acetate. After vigorous mixing the organic phase was separated, and the aqueous phase was extracted again with ethyl acetate. The combined organic phases were washed with water and evaporated. The residue was taken up in toluene and recrystallized from toluene/ethanol. 12.4 g of crude product were obtained. This was purified by flash chromatography on 500 g silica gel, using cyclohexane/ethyl acetate as the eluent, first in the ratio 1:1 then in the ratio 4:6. Crystallization of the resulting product from ethanol resulted in 4.4 g of 3-hydroxyimino-1-methyl-2-oxo-5-cyclohexyl-2,3-dihydro-1H-1,4-benzodiazepine having a melting point of 205–210° C.

(E) 4.4 g of the product obtained above were added to a mixture of 375 ml of glacial acetic acid and 42.3 ml of trifluoroacetic acid. The reaction mixture was heated to 40° C. (internal temperature), and a total of 2.36 g of zinc dust was added in portions while stirring. The mixture was stirred at 40° C. for a further 2 hours, and then another 1.1 g of zinc dust were added, and the mixture was stirred at 40° C. for an additional 1.5 hours. The mixture was worked up by diluting with toluene, allowing it to cool and evaporating the solvent. The remaining residue was taken up in dichloromethane, washed with aqueous sodium carbonate solution and water, dried and evaporated. 4.0 g of crude 3-amino-1-methyl-2-oxo-5-cyclohexyl-2,3-dihydro-1H-1,4benzodiazepine were obtained and were further processed without purification in the subsequent reaction stage.

(F) 2.92 g of 4H-pyrrolo[3,2,1-ij]-5,6-dihydroquinoline-2-carboxylic acid (obtained as in Example 1F to 1G) and 1.99 ml of triethylamine were dissolved in 64 ml of dichloromethane. The solution was cooled to −20° C. and, while stirring, 1.13 ml of methanesulfonyl chloride were slowly added dropwise, and the reaction mixture was stirred at −20° C. for a further 15 minutes. A solution of 4.0 g of the 3-amino-1-methyl-2-oxo-5-cyclohexyl-2,3-dihydro-1H-1,4-benzodiazepine obtained in stage E and 1.99 ml of triethylamine in 54 ml of dichloromethane was added dropwise at a temperature between −15 and −20° C. to the stirred reaction solution containing the mixed anhydride from methanesulfonic acid and 4H-pyrrolo[3,2,1-ij]-5,6-dihydroquinoline-2-carboxylic acid, and the reaction mixture was stirred at −15° C. for a further 30 minutes and allowed to warm slowly (within one hour) to room temperature. The reaction mixture was worked up by diluting with water, separating the dichloromethane phase, washing with sodium bicarbonate and then with water, drying over sodium sulfate, filtering, and evaporating the solvent. 7.6 g of the crude title compound were obtained as a residue. The crude product was purified by column chromatography on 400 g of silica gel under slightly elevated pressure (flash chromatography) using cyclohexane/ethyl acetate 1:1 as the eluent. The purified product was crystallized from ethanol and dried. 1.5 g of 3-[(4H-pyrrolo[3,2,1-ij]-5,6-dihydroquinoline-2-carbonyl)-amino]-1-methyl-2-oxo-5-cyclohexyl-1H-2,3-dihydro-1,4-benzodiazepine having a melting point of 147–152° C. were obtained.

EXAMPLE 5

3-[(8-Fluoro-4H-pyrrolo[3,2,1-ij]-5,6-dihydroquinoline-2-carbonyl)-amino-2-oxo-1-methyl-5-phenyl-1H-2,3-dihydro-1,4-benzodiazepine.

0.99 g of 8-fluoro-4H-pyrrolo[3,2,1-ij]-5,6-dihydroquinoline-2-carboxylic acid, 1.4 g of 2-chloro-1-methylpyridinium iodide, 1.1 ml of triethylamine and 1.2 g of 3-amino-2-oxo-1-methyl-5-phenyl-2,3-dihydro-1H-1,4-benzodiazepine were dissolved in 120 ml of dichloromethane, and the reaction mixture was boiled to reflux for 1 hour. The reaction mixture was worked up by allowing it to cool, adding 5% strength sodium bicarbonate solution, separating the organic phase, and extracting the aqueous phase again with dichloromethane. The combined dichloromethane extracts were dried over sodium sulfate, and the solvent was distilled off under reduced pressure. The crude title compound remaining as a residue was purified by column chromatography on silica gel using dichloromethane/methanol 99:1. 1.5 g of 3-[(8-fluoro-4H-pyrrolo[3,2,1-ij]-5,6-dihydroquinoline-2-carbonyl)-amino]-2-oxo-1-methyl-5-phenyl-1H-2,3-dihydro-1,4-benzodiazepine having a melting point of 181–182° C. were obtained.

EXAMPLE 6

3-[(4H-Pyrrolo[3,2,1-ij]-5,6-dihydroquinoline-2-carbonyl)-amino]-1-methyl-2-oxo-5-phenyl-1H-2,3-dihydro-1,4-benzodiazepine.

(A) 98.6 g of 2-aminobenzophenone were dissolved in a mixture of 650 ml of dichloromethane and 50 ml of water. A solution of 116.1 g of bromoacetyl bromide in 150 ml of dichloromethane was added dropwise to this mixture at a temperature of −10° C. The reaction mixture was then stirred at room temperature for a further 2 hours. The reaction mixture was worked up by adding water, separating the organic phase, washing again with water, drying and evaporating under reduced pressure. The crude product remaining as a residue was crystallized from ether/petroleum ether. 142 g of 2-[(2-bromoacetyl)-amino]-benzophenone having a melting point of 96–98° C. were obtained.

(B) 71 g of the 2-[(2-bromoacetyl)-amino]-benzophenone obtained above were dissolved in 500 ml of methanol. A solution of 75 g of ammonia in 1.2 l of methanol was added dropwise to this solution at a temperature of 10° C. Then the reaction mixture was first stirred at room temperature for 1.5 hours and then heated to reflux for 2 hours. The reaction mixture was worked up by distilling off the methanol under reduced pressure, dissolving the residue in dichloromethane, washing the solution with 10% strength aqueous sodium hydroxide solution and with water, drying and concentrating under reduced pressure. The crude product remaining as residue was crystallized from methanol. 20 g of 2-oxo-5-phenyl-1H-2,3-dihydro-1,4-benzodiazepine having a melting point of 178–180° C. were obtained.

(C) 60 g of the product obtained above were dissolved in 1.2 l of dried tetrahydrofuran. While excluding moisture, 34.2 g of potassium tert.-butylate were added to the solution. A solution of 20.6 ml of methyl iodide in 75 ml of tetrahydrofuran was then added dropwise, and the reaction mixture was stirred at room temperature for a further hour. To work up the reaction mixture, ice-cold sodium chloride solution was added; the reaction mixture was diluted with dichloromethane; the aqueous phase was separated, and the organic phase was washed with water to neutrality, dried over sodium sulfate, filtered and evaporated. The crude product obtained as a residue was recrystallized from ethanol. 56 g of 1-methyl-2-oxo-5-phenyl-1H-2,3-dihydro-1,4-benzodiazepine having a melting point of 154–155° C. were obtained.

(D) 50.4 g of the product obtained above were added to 987 ml of toluene, cooled to −20° C. and reacted with 56.4 g of potassium tert.-butylate and 32.3 ml of isoamyl nitrite by the method described in Example 1 (D). The reaction mixture was worked up as described in Example 1 (D), and the resulting crude product was crystallized from ethanol. 47.2 g of 3-hydroxyimino-1-methyl-2-oxo-5-phenyl-2,3-dihydro-1H-1,4-benzodiazepine having a melting point of 239–242° C. were obtained.

(E) 6.8 g of the product obtained above were dissolved in 500 ml of methanol. 12 g of Raney nickel were added to the solution which was then hydrogenated at room temperature under a hydrogen pressure of 6 bar for 12 hours. To work up the reaction solution, the catalyst was filtered out, and the solvent was removed by distillation under reduced pressure. 6 g of crude racemic 3-amino-1-methyl-2-oxo-5-phenyl-2,3-dihydro-1H-1,4-benzodiazepine were obtained. This product was dissolved in 50 ml of acetonitrile for further purification by conversion into its benzenesulfonate salt. A solution of 3.6 g of benzenesulfonic acid in 22 ml of acetonitrile was added to the solution, and the reaction mixture was stirred at room temperature for one hour. The crystalline precipitate which formed was filtered out with suction, washed with acetonitrile and then with hexane, and then dried under reduced pressure. 5.9 g of the benzenesulfonate of the 3-amino compound having a melting point of 224–227° C. were obtained. To liberate the amine, 5 g of the benzenesulfonate salt obtained above were dissolved in dichloromethane, and the solution was shaken with aqueous sodium carbonate solution. The dichloromethane phase containing the liberated amine compound was separated, dried and evaporated. 3.1 g of 3-amino-1-methyl-2-oxo-5-phenyl-2,3-dihydro-1H-1,4-benzodiazepine were obtained.

(F) 0.38 g of 4H-pyrrolo[3,2,1-ij]-5,6-dihydroquinoline-2-carboxylic acid, 0.50 g of 3-amino-1-methyl-2-oxo-5-phenyl-2,3-dihydro-1H-1,4-benzodiazepine and 0.46 g of triethylamine were dissolved in 50 ml of dichloromethane. 0.58 g of 2-chloro-1-methylpyridinium iodide was added to the solution, and the reaction mixture was boiled to reflux for one hour. The reaction mixture was then worked up as described in Example 5. 0.69 g of 3-[(4H-pyrrolo[3,2,1-ij]-5,6-dihydroquinoline-2-carbonyl)-amino]-1-methyl-2-oxo-5-phenyl-1H-2,3-dihydro-1,4-benzodiazepine was obtained as a resinous foam. $^{13}$C NMR spectrum: [data in ppm, (signal multiplicity)]

167.88 (s), 167.51 (s), 162.32 (s), 142.91 (s), 138.17 (s), 136.40 (s), 131.93 (d), 130.72 (d), 130.69 (d), 130.23 (s), 129.83 (d), 129.83 (d), 129.22 (s), 128.28 (d), 128.28 (d), 124.58 (d), 124.40 (s), 123.09 (s), 121.60 (d), 120.90 (d), 120.66 (d), 119.34 (d), 104.24 (d), 67.40 (d), 44.38 (t), 35.36 (q), 24.89 (t), 23.13 (t).

EXAMPLE 7

Preparation of the optical isomers of 3-[(4H-pyrrolo[3,2,1-ij]-5,6-dihydroquinoline-2-carbonyl)-amino]-1-methyl-2-oxo-5-phenyl-1H-2,3-dihydro-1,4-benzodiazepine.

7a: (−)-(3S)-3-[(4H-Pyrrolo[3,2,1-ij]-5,6-dihydroquinoline-2-carbonyl)-amino]-1-methyl-2-oxo-5-phenyl-1H-2,3-dihydro-1,4-benzodiazepine.

(A) Analogously to Example 2a A–D, (−)-(3S)-3-amino-1-methyl-2-oxo-5-phenyl-1H-2,3-dihydro-1,4-benzodiazepine having an optical rotation $[\alpha]_D^{20}$ of −230.8° (c=1 in acetonitrile) was produced from racemic 3-amino-1-methyl-2-oxo-5-phenyl-2,3-dihydro-1H-1,4-benzodiazepine (for preparation, see Example 6 (E).

(B) Analogously to the method described in Example 1H, 1.7 g of the (−)-(3S)-3-amino-1-methyl-2-oxo-5-phenyl-2,3-dihydro-1H-1,4-benzodiazepine obtained above were reacted with a reaction solution containing the mixed anhydride from 1.36 g of 4H-pyrrolo-[3,2,1-ij]-5,6-dihydroquinoline-2-carboxylic acid and 0.52 ml of methanesulfonyl chloride in dichloromethane. The reaction mixture was worked up as described in Example 1 H). 2.6 g of crystalline product purified by flash chromatography were obtained. This was recrystallized from methanol to remove enantiomeric impurities. 1.4 g of enantiomerically pure (−)-(3S)-3-[(4H-pyrrolo[3,2,1-ij]-5,6-dihydroquinoline-2-carbonyl)-amino]-1-methyl-2-oxo-5-phenyl-1H-2,3-dihydro-1,4-benzodiazepine having a melting point of 151-158° C. and an optical rotation $[\alpha]_D^{20}$ of −61.6° (c=0.5 in methanol) were obtained.

7b: (+)-(3R)-3-[(4H-Pyrrolo[3,2,1-ij]-5,6-dihydroquinoline-2-carbonyl)-amino]-1-methyl-2-oxo-5-phenyl-1H-2,3-dihydro-1,4-benzodiazepine.

(A) (+)-(3R)-3-amino-1-methyl-2-oxo-5-phenyl-2,3-dihydro-1H-1,4-benzodiazepine with an optical rotation $[\alpha]_D^{20}$ of +259.1° (c=1 in acetonitrile) was produced in a manner analagous to Example 2b A–C.

(B) Analogous to the method described in Example 1 H), 0.65 g of the (+)-(3R)-3-amino-1-methyl-2-oxo-5-phenyl-2,3-dihydro-1H-1,4-benzodiazepine obtained above was reacted with a reaction solution containing the mixed anhydride from 0.52 g of 4H-pyrrolo[3,2,1-ij]-5,6-dihydroquinoline-2-carboxylic acid and 0.2 ml of methanesulfonyl chloride in dichloromethane. The reaction mixture was worked up as described in Example 1 (H). Flash chromatography and crystallization from ethanol resulted in 596 mg of enantiomerically pure (+)-(3R)-3-[(4H-pyrrolo[3,2,1-ij]-5,6-dihydroquinoline-2-carbonyl)-amino]-1-methyl-2-oxo-5-phenyl-1H-2,3-dihydro-1,4-benzodiazepine having a melting point of 147-156° C.

Optical rotation $[\alpha]_D^{20}$= +61.0° (c=0.5 in methanol).

EXAMPLE 8

3-[(4H-Pyrrolo[3,2,1-ij]-5,6-dihydroquinoline-2-carbonyl)-amino]-1,7-dimethyl-2-oxo-5-(2-thienyl)-1H-2,3-dihydro-1,4-benzodiazepine.

(A) 30 g of $N_1$-methyl-$N_1$-(4-methylphenyl)-2-hydroxy-1,3-diaminopropane and 24.2 ml of triethylamine were dissolved in 225 ml of dichloromethane. A solution of 16.5 ml of thiophene-2-carbonyl chloride in 50 ml of dichloromethane was slowly added dropwise to the solution while cooling in ice. The reaction mixture was allowed to stand at room temperature for 12 hours. The reaction solution was then worked up by washing with water and aqueous sodium chloride solution, separating and drying the organic phase, and removing the solvent by distillation under reduced pressure. The residue obtained was 52.2 g of crude oily $N_1$-methyl-$N_1$-(4-methylphenyl) -$N_2$-(2-thienoyl) -2-hydroxy-1,3-diaminopropane, which was employed without further purification in the next reaction stage.

(B) 50.2 g of the product obtained above were added to 150 ml of phosphorus oxychloride, and the reaction mixture was heated at reflux for 90 minutes. It was then cooled and worked up as described in Example 1 (B). 48.5 g of an oily crude product were obtained which contained a mixture of 2-chloromethyl-1,7-dimethyl-5-(2-thienyl)-2,3-dihydro-1H-1,4benzodiazepine and 3-chloro-1,8-dimethyl-6-(2-thienyl)-1,2,3,4-tetrahydro-1,5-benzodiazocine. To isomerize the benzodiazocine fraction, the crude mixture was dissolved in 280 ml of tetrachloroethane and heated at reflux for one hour. The tetrachloroethane was then evaporated off, the residue was dissolved in dichloromethane, and the solution was washed with 10% strength sodium hydroxide solution and then with water and with aqueous sodium chloride solution, dried and evaporated under reduced pressure. The remaining residue was dissolved in a mixture of methylene chloride and methanol, and the solution was filtered through magnesium silicate (=Florisil ®) and reduced in volume. 32.4 g of 2-chloromethyl-1,7-dimethyl-5-(2-thienyl)-2,3-dihydro-1H-1,4-benzodiazepine were obtained as an oily substance which was further processed without further purification in the next reaction stage.

(C) 13.6 g of the substance obtained above were oxidized with 8.2 g of potassium permanganate by the method described in Example 1C. The reaction mixture was worked up as described in Example 1 (C). The resulting crude product was dissolved in dichloromethane and purified by flash chromatography on silica gel using dichloromethane/methanol 95:5 as the eluent. 3.8 g of oily 1,7-dimethyl-2-oxo-5-(2-thienyl)-2,3-dihydro-1H-1,4-benzodiazepine were obtained.

(D) 7.7 g of the product obtained above were dissolved in 210 ml of toluene. After cooling to −20° C., 8.1 g of potassium tert.-butylate were added under an $N_2$ atmosphere, and the mixture was stirred for a further 15 minutes. Then 4.6 ml of isoamyl nitrite were added, while cooling, at such a rate that the temperature of the reaction mixture remained below 0° C. The mixture was then stirred at 0° C. for a further 30 minutes. For working up, the reaction mixture was added to a stirred mixture of 300 ml of ice-cold water, 300 ml of ethyl acetate and 15 ml of glacial acetic acid. The organic phase was separated, and the aqueous phase was extracted again with ethyl acetate. The organic phases were combined, washed with water and with aqueous sodium chloride solution, dried over sodium sulfate and concentrated under reduced pressure. 6.5 g of 3-hydroxyimino-1,7-dimethyl-2-oxo-5-(2-thienyl)-2,3-dihydro-1H-1,4-benzodiazepine were obtained as a resinous foam.

(E) 2.0 g of the product obtained above were dissolved in 150 ml of methanol. 8 g of Raney nickel were added, and the mixture was then hydrogenated with a hydrogen pressure of 4 bar for 7.5 hours. The reaction was worked up by filtering out the catalyst and distilling off the solvent under reduced pressure. 1.4 g of crude product remained as a residue. This was taken up in dichloromethane and extracted with dilute aqueous hydrochloric acid solution. The hydrochloric acid phase was separated, made alkaline by addition of dilute aqueous sodium hydroxide solution and extracted with dichloromethane. Evaporation of the dichloromethane extract resulted in 0.7 g of 3-amino-1,7-dimethyl-2-oxo-5-(2-thienyl)-2,3-dihydro-1H-1,4benzodiazepine as a resinous foam, which was further processed without purification in the following reaction stage.

(F) Analogously to the method described in Example 1 (H), 1.15 g of the 3-amino-1,7-dimethyl-2-oxo-5-(2-thienyl)-2,3-dihydro-1H-1,4-benzodiazepine obtained above were reacted with a reaction solution containing the mixed anhydride from 0.81 g of 4H-pyrrolo[3,2,1-ij]-5,6-dihydroquinoline-2-carboxylic acid and 0.32 ml of methanesulfonyl chloride in dichloromethane. The reaction mixture was worked up as described in Example 1 (H). 2.3 g of crude product were obtained and were dissolved in dichloromethane and purified by flash chromatography on silica gel using dichloromethane/methanol 96:4 as the eluent. Removal of the solvent by distillation resulted in 0.7 g of residue which was crystallized from a mixture of cyclohexane and ethyl acetate. 0.4 g of crystalline 3-[(4H-pyrrolo[3,2,1-ij]-5,6-dihydroquinoline-2-carbonyl)-amino]-1,7-dimethyl-2-oxo-5-(2-thienyl)-1H-2,3-dihydro-1,4-benzodiazepine having a melting point of 204–207° C. were obtained.

The compounds of formula I listed in the following table were also obtained by the processes described in the foregoing examples by acylation of the corresponding 3-aminobenzodiazepine derivatives of formula II.

| Ex. No. | $R^1$ | $R^2$ | $R^3$ | $R^4$ = phenyl substituted by $R^7$ and $R^8$ | | Z | $R^5$ | $R^6$ | Notes |
|---|---|---|---|---|---|---|---|---|---|
| | | | | $R^7$ | $R^8$ | | | | |
| 9  | $CH_3$—        | 8-$OCH_3$ | H | 2-F      | H    | —$(CH_2)_3$—            | H  | H         | resinous foam |
| 10 | $CH_3$—        | 7-$CH_3$  | H | 2-F      | H    | —$(CH_2)_3$—            | H  | H         | m.p. 154–157 |
| 11 | $CH_3$—        | H         | H | 2-F      | 4-F  | —$(CH_2)_3$—            | H  | H         | m.p. 231–234 |
| 12 | $CH_3$—        | H         | H | H        | H    | —$CH_2)_3$—             | Cl | H         | resinous foam |
| 13 | $CH_3$—        | 8-$OCH_3$ | H | 2-F      | 6-F  | —$(CH_2)_3$—            | H  | H         | m.p. 209–210 |
| 14 | $CH_3$—        | 8-$OCH_3$ | H | 2-O-ipen | 4-F  | —$(CH_2)_3$             | H  | H         | m.p. 188–192 |
| 15 | $CH_3$—        | 8-$OCH_3$ | H | 2-F      | 4-F  | —$CH_2)_3$—             | H  | H         | m.p. 222–225 |
| 16 | $CH_3$—        | 8-$OCH_3$ | H | 3-Cl     | 4-Cl | —$(CH_2)_3$—            | H  | H         | m.p. 207–209 |
| 17 | $CH_3$—        | 8-$OCH_3$ | H | 2-O-ipen | 6-F  | —$(CH_2)_3$—            | H  | H         | m.p. 176–178 |
| 18 | $CH_3$—        | 7-$CH_3$  | H | H        | H    | —$(CH_2)_3$—            | H  | H         | m.p. 231–238 |
| 19 | $CH_3$—        | H         | H | 3-Cl     | 4-Cl | —$(CH_2)_3$—            | H  | H         | m.p. 273–277 |
| 20 | $CH_3$—        | H         | H | 2-F      | 6-F  | —$(CH_2)_3$—            | H  | H         | m.p. 254–257 |
| 21 | $CH_3$—        | H         | H | 2-O-ipen | 6-F  | —$(CH_2)_3$—            | H  | H         | m.p. 201–205 |
| 22 | $CH_3$—        | H         | H | 2-F      | H    | —$(CH_2)_3$—            | H  | H         | m.p. 246–251 |
| 23 | cycpr-$CH_2$—  | H         | H | H        | H    | —$(CH_2)_3$—            | H  | H         | m.p. 145–147 |
| 24 | $CH_3$—        | 7-$CH_3$  | H | 2-O-ipen | H    | —$(CH_2)_3$—            | H  | H         | m.p. 189–192 |
| 25 | $(CH_3)_2CH$—  | H         | H | H        | H    | —$CH_2)_3$—             | H  | H         | m.p. 135–140 |
| 26 | $CH_3$—        | 7-Cl      | H | H        | H    | —$(CH_2)_3$—            | H  | 8-F       | m.p. 263–264 |
| 27 | $CH_3$—        | 7-$CH_3$  | H | 3-Cl     | 4-Cl | —$(CH_2)_3$—            | H  | H         | m.p. 173–200 S |
| 28 | $CH_3$—        | 7-$CH_3$  | H | 2-O-ipen | 6-F  | —$(CH_2)_3$—            | H  | H         | m.p. 178–181 |
| 29 | $CH_3$—        | 7-$CH_3$  | H | 2-O-ipen | 4-F  | —$(CH_2)_3$—            | H  | H         | m.p. 184–188 |
| 30 | $CH_3$—        | H         | H | 4-$CH_3$ | H    | —$(CH_2)_3$—            | H  | H         | m.p. 148–152 |
| 31 | $CH_3$—        | H         | H | H        | H    | —$(CH_2)_3$—            | H  | 8-$OCH_3$ | m.p. 252–256 |
| 32 | $CH_3$—        | H         | H | H        | H    | —$(CH_2)_3$—            | H  | 9-Cl      | m.p. 176–179 |
| 33 | $CH_3$—        | H         | H | H        | H    | —$(CH_2)_2$—            | H  | H         | m.p. 193–197 |
| 34 | $CH_3$—        | H         | H | H        | H    | —$(CH_2)_2$—$C(CH_3)_2$— | H | H         | m.p. 196–200 |
| 35 | $CH_3$—        | H         | H | H        | H    | —$(CH_2)_4$—            | H  | H         | m.p. 236–239 |
| 36 | $CH_3$—        | H         | H | H        | H    | -pheneth-               | H  | H         | oil |
| 37 | $CH_3$—        | H         | H | H        | H    | —$(CH_2)_2$—O—          | H  | H         | m.p. 214–214 |
| 38 | $CH_3$—        | H         | H | H        | H    | —$(CH_2)_2$—S—          | H  | H         | m.p. 255–259 | ipen = isoamyl;
cycpr = cyclopropyl;
pheneth = phen-1-yl-2-ethylene;
m.p. = melting point in °C.;
S = sintering.

EXAMPLE I

Tablets containing 3-[(4H-pyrrolo[3,2,1-ij)-5,6-dihydroquinoline-2-carbonyl)-amino]-8-methoxy-1-methyl-2-oxo-5-phenyl-1H-2,3-dihydro-1,4-benzodiazepine.

Tablets were prepared containing, per tablet:

| | |
|---|---:|
| 3-[(4H-pyrrolo[3,2,1-ij)-5,6-dihydroquinoline-2-carbonyl)-amino]-8-methoxy-1-methyl-2-oxo-5-phenyl-1H-2,3-dihydro-1,4-benzodiazepine | 20 mg |
| maize starch | 60 mg |
| lactose | 135 mg |
| gelatin (as 10% strength solution) | 6 mg |

The active substance, the maize starch and the lactose were thickened with the 10% strength gelatin solution. The paste was comminuted, and the resulting granules were placed on a suitable metal sheet and dried at 45° C. The dried granules were passed through a comminuting machine and mixed with the following additional adjuvants in a mixer:

| | |
|---|---|
| talc | 5 mg |
| magnesium stearate | 5 mg |
| maize starch | 9 mg | and then compressed to form 240 mg tablets.

EXAMPLE II

Tablets containing 3-[(4H-pyrrolo[3,2,1-ij)-5,6-dihydroquinoline-2-carbonyl)-amino]-8-methoxy-1-methyl-2-oxo-5-phenyl-1H-2,3-dihydro-1,4-benzodiazepine.

Tablets with the following composition per tablet were prepared in analogy to Example I:

| | |
|---|---|
| 3-[(4H-pyrrolo[3,2,1-ij)-5,6-dihydroquinoline-2-carbonyl)-amino]-8-methoxy-1-methyl-2-oxo-5-phenyl-1H-2,3-dihydro-1,4-benzodiazepine. | 20 mg |
| maize starch | 60 mg |
| lactose | 135 mg |
| gelatin (as 10% strength solution) | 6 mg |
| talc | 5 mg |
| magnesium stearate | 5 mg |
| maize starch | 9 mg |

The foregoing description and examples have been set forth merely to illustrate the invention and are not intended to be limiting. Since modifications of the described embodiments incorporating the spirit and substance of the invention may occur to persons skilled in the art, the scope of the invention should be construed to include all variations falling within the ambit of the appended claims and equivalents thereof.

What is claimed is:

1. A compound corresponding to the formula I

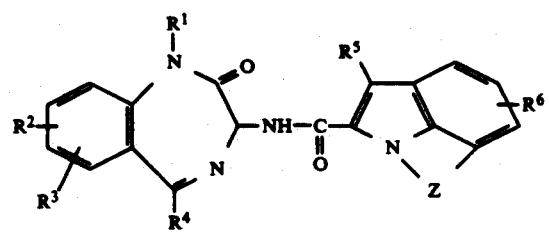

wherein
$R^1$ represents hydrogen, lower alkyl or cycloalkylalkyl with 4–7 carbon atoms,
$R^2$ represents hydrogen, halogen, lower alkyl, lower alkoxy or trifluoromethyl, and
$R^3$ represents hydrogen, halogen, lower alkyl or lower alkoxy, or $R^2$ and $R^3$ are bonded to two adjacent carbon atoms and together denote an alkylenedioxy group with 1–2 carbon atoms,
$R^4$ represents cycloalkyl with 5 to 6 carbon atoms, thiophene or an optionally substituted phenyl group a

in which
$R^7$ represents hydrogen, halogen, lower alkyl, lower alkoxy or trifluoromethyl, and
$R^8$ represents hydrogen, halogen, lower alkyl or lower alkoxy,
$R^5$ represents hydrogen or halogen,
$R^6$ represents hydrogen, halogen, lower alkyl, lower alkoxy or trifluoromethyl, and
Z represents an alkylene chain with 2–4 carbon atoms, which can optionally be mono- or disubstituted by lower alkyl, or onto which a 5–6-membered carbocyclic ring can optionally be fused, or represents a —X—CH$_2$—CH$_2$—chain in which X is bonded to the phenyl ring of the indole structure and represents oxygen or sulfur,
and the pharmaceutically acceptable acid addition salts thereof.

2. A compound according to claim wherein $R^5$ represents hydrogen, and Z represents a propylene chain.

3. A compound according to claim 1, wherein $R^4$ represents an optionally substituted phenyl group a in which $R^7$ and $R^8$ have the above meanings.

4. A compound according to claim 3, wherein Z represents an alkylene chain with 2–3 carbon atoms; $R^2$ represents hydrogen, lower alkoxy, lower alkyl, or halogen; $R^3$ represents hydrogen; $R^7$ represents hydrogen, lower alkyl, or halogen; $R^8$ represents hydrogen or halogen; $R^5$ represents hydrogen; and $R^6$ represents hydrogen or halogen.

5. A compound according to claim 4, wherein $R^2$ represents methoxy, methyl or chlorine; $R^7$ represents methyl or fluorine, and $R^8$ represents fluorine.

6. 3-[(4H-Pyrrolo[3.2.1-ij]-5,6-dihydroquinoline-2-carbonyl)-amino]-8-methoxy-1-methyl-2-oxo-5-phenyl-1H-2,3-dihydro-1,4-benzodiazepine and the acid addition salts and optical isomers thereof.

7. A compound according to claim 2, wherein $R^2$ represents hydrogen, lower alkoxy, lower alkyl, or halogen, and $R^3$ represents hydrogen, $R^4$ represents cycloalkyl with 5–6 carbon atoms or thienyl, and $R^6$ represents hydrogen or halogen.

8. A compound according to claim 7, wherein $R^2$ is selected from the group consisting of methoxy, methyl, and chlorine.

9. A compound according to claim 6, wherein $R^4$ represents cyclohexyl.

10. A pharmaceutical composition comprising an effective CCK antagonizing amount of a compound according to claim 1, and at least one conventional pharmaceutical adjuvant or carrier.

* * * * *